(12) United States Patent
Lareida

(10) Patent No.: US 7,338,955 B1
(45) Date of Patent: Mar. 4, 2008

(54) MEDICAMENT FOR TREATMENT OF NEUROPATHIES

(75) Inventor: Juerg Lareida, Aarau (CH)

(73) Assignee: Lilly ICOS LLC, Wilmington, DE (US)

( * ) Notice: Subject to any disclaimer, the term of this patent is extended or adjusted under 35 U.S.C. 154(b) by 0 days.

(21) Appl. No.: 10/088,113

(22) PCT Filed: Jul. 27, 2000

(86) PCT No.: PCT/CH00/00409

§ 371 (c)(1),
(2), (4) Date: Mar. 15, 2002

(87) PCT Pub. No.: WO01/26659

PCT Pub. Date: Apr. 19, 2001

(30) Foreign Application Priority Data

Oct. 12, 1999 (CH) .................. 1862/99

(51) Int. Cl.
*A61K 31/497* (2006.01)
*A61K 31/517* (2006.01)
*A61K 31/519* (2006.01)

(52) U.S. Cl. .............. 514/252.16; 514/258.1

(58) Field of Classification Search .......... 514/258
See application file for complete search history.

(56) References Cited

U.S. PATENT DOCUMENTS

| 4,666,908 | A |   | 5/1987 | Hamilton | |
|---|---|---|---|---|---|
| 5,753,225 | A | * | 5/1998 | Clary et al. | 424/130.1 |
| 5,972,342 | A | * | 10/1999 | Rakoto Ratsimamanga et al. | 424/776 |
| 6,037,346 | A | * | 3/2000 | Doherty et al. | 514/252.03 |
| 6,075,028 | A |   | 6/2000 | Graham | |
| 6,277,884 | B1 | * | 8/2001 | de Tejada | 514/565 |
| 6,399,601 | B1 | * | 6/2002 | Du Bois | 514/233.8 |
| 2002/0119974 | A1 | * | 8/2002 | Laties | 514/234.5 |
| 2003/0104993 | A1 | * | 6/2003 | Rueger et al. | 514/12 |

FOREIGN PATENT DOCUMENTS

WO  WO 93/07149  4/1993

OTHER PUBLICATIONS

Database EMBASE in ACS. Accession No. 84123090, Gentile et al. Diabetic neuropathy, II. Autonomic neuropathy. The gastro-intestinal system. Minerva Medica, 1984 75/14-15 (783-790), abstract.*
Dorland's Illustrated Medical Dictionary, 1994 p. 1132.*
H.G. Nurnberg et al., *J. Clin. Psychiatry*, 60:1, pp. 33-35 (1999).
M. Brewer et al., *Movement Disorders*, Bd. 13, Nr. 5 (1998).
T.A. Zesiewicz et al., *Neurology*, Bd. 52, Nr. 6 (1999).
D.M. Swope, *Neurology*, Bd. 54, Nr. 7 (2000).
M.S. Rendell et al., *JAMA, The Journal of the American Medical Association*, vol. 281, No. 5 pp. 421-426 (1999).

* cited by examiner

*Primary Examiner*—Jennifer Kim
(74) *Attorney, Agent, or Firm*—Marshall, Gerstein & Borun LLP

(57) ABSTRACT

Compounds of formula (I) in which $R^1=C_{1-6}$ alkyl, optionally halosubstituted; $R^2$=H, $C_{1-4}$ alkyl, optionally halosubstituted or replaced by halogen; $R^3=C_{2-4}$ alkyl, optionally halosubstituted; $R^4=SO_2NR^5R^{\&}$, $CO_2R^7$ or halogen, $C_{2-4}$ alkenyl; optionally substituted with $NR^5R^6$, $SONR^5R^6$, $CONR^5R^6$, $CO^2R^7$ or halogen, $C_{2-4}$ alkanoyl, optionally substituted with $NR^5R^6$, $SONR^5R^6$, $CONR^5R^6$, $CO_2R^7$ or halogen; $R^5$ and $R^6$=independently H or $C^{1-4}$ alkyl, or, together with the N atom to which they are attached, a pyrrolidino, piperidino, morpholino, 4-($NR^8$)-1-piperazinyl or 1-imidazolyl ring optionally substituted with one or two $C_{1-4}$ alkyl groups; $R^7$=H, $C^{1-4}$ alkyl, optionally fluorosubstituted, and $R^8$=H,$C^{1-3}$ alkyl or hydroxyalkyl with 1-4 C atoms, or the pharmaceutically acceptable salts thereof are useful for the chemotherapeutic treatment of neuropathies.

7 Claims, No Drawings

MEDICAMENT FOR TREATMENT OF NEUROPATHIES

CROSS REFERENCE TO RELATED APPLICATION

This is a National Phase patent application based on PCT/CH00/00409 filed 27 Jul. 2000 which in turn claims priority of Swiss Application No. 1862/99 filed 12 Oct. 1999, the subject matter of which is incorporated herein by reference.

FIELD AND SUMMARY OF THE INVENTION

The present invention relates to pharmaceutical agents for treatment of neuropathies, such as, e.g., peripheral diabetic polyneuropathies and gastropareses, as well as general degenerative, toxic, metabolic, ischemic and other autonomous forms of neuropathies in the narrower, namely neurological sense.

Surprisingly, it has been found that compounds of formula (I)

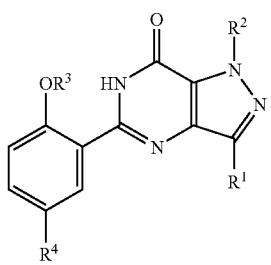

known, for example, from WO 93/07149 as such and for use as a pharmaceutical agent for cardiovascular disorders, in which $R^1 = C_{1-6}$alkyl, optionally substituted by halogen, $R^2 =$ hydrogen or $C_{1-4}$alkyl, optionally substituted by halogen, $R^3 = C_{2-4}$alkyl, optionally substituted by halogen, $R^4 = SO_2NR^5R^6$, $C_{1-4}$alkyl, optionally substituted with $NR^5R^6$, CN, $CONR^5R^6$, $CO_2R^7$, or halogen, $C_{2-4}$-alkenyl, optionally substituted with $NR^5R^6$, $SONR^5R^6$, $CONR^5R^6$, $CO_2R^7$, or halogen, $C_{2-4}$-alkanoyl, optionally substituted with $NR^5R^6$, $SONR^5R^6$, $CONR^5R^6$, $CO_2R^7$, or halogen, $R^5$ and $R^6$, independent of one another, represent hydrogen or $C_{1-4}$alkyl, or, together with the nitrogen atom to which they are attached, represent a pyrrolidino, piperidino, morpholino, 4-($NR^8$)-1-piperazinyl or 1-imidazolyl ring which, optionally, may be substituted with one or two $C_{1-4}$alkyl groups, $R^7 =$ hydrogen or $C_{1-4}$alkyl, and $R^8 =$ hydrogen, $C_{1-3}$alkyl, or hydroxy alkyl with 1-4 C atoms, as well as pharmaceutically acceptable salts of such compounds (I), are suitable for chemotherapeutic treatment of neuropathies of the type mentioned above.

In the above definitions, halogen represents fluorine, chlorine, or bromine, fluorine being preferred.

Compounds which correspond or are analogous to this formula, including its salts, and preparation processes of such compounds and salts are known in the art, e.g. from EP 0 463 756, where, they have been proposed for prophylactic or therapeutic treatment of cardiovascular diseases. The cardiovascular activity of formula (I) compounds is based on the fact that these compounds are effective and selective inhibitors for cyclic 3',5'-monophosphate phosphodiesterase (cGMP PDE).

It is not known and—respectively—is improbable on the basis of what is known, that this inhibitor effect plays a significant role in neuropathies of the type mentioned. Also, the efficacy of formula (I) compounds for treatment of neuropathies has, in fact, not been determined on the basis of theoretical considerations, but in an empirical manner, and was neither anticipated nor predictable.

DESCRIPTION OF PREFERRED EMBODIMENTS

Accordingly, the present invention, in a first embodiment, has for its object a pharmaceutical agent for treatment of neuropathies, characterized in that it consists, at least in part, of at least one compound of formula (I), or at least one pharmaceutically acceptable salt of such a compound, and that it may contain standard auxiliary agents, adjuvants, and carriers, as well as, optionally, additional pharmaceutically active substances.

In accordance with a further embodiment, the invention pertains to the use of compounds of formula (I) and/or their pharmaceutically acceptable salts for therapeutic treatment of neuropathies of the type mentioned above.

Examples of pharmaceutically acceptable salts of compounds and additional methods of synthesis are also known from the above-noted EP 0 463 756 and, furthermore, from WO 93/07149, as well as from WO 93/06104 and WO 94/05661.

For production of pharmaceutical agents according to the invention, active agents of formula I may be formulated as solid or liquid products with standard adjuvants and carrier substances.

In a preferred group of compounds (I), $R^4$ represents a group of formula (II):

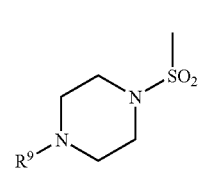

particularly if $R^1$, $R^2$, $R^3$, and $R^9$, respectively, represent alkyl groups with 1-4 C atoms, preferably, methyl or ethyl, which, optionally, may be substituted or replaced by halogen, preferably, fluorine.

Such compounds correspond to formula (Ia):

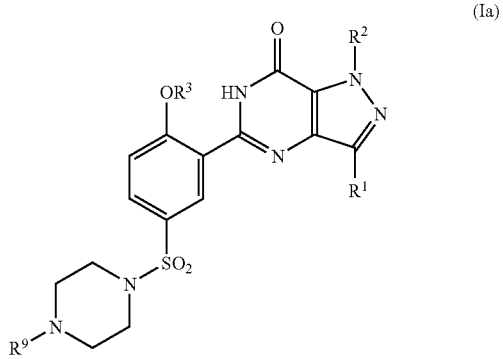

in which groups $R^1$ to $R^3$ and $R^9$ have the above-specified meaning.

A preferred specific compound for pharmaceutical agents in accordance with the invention corresponds to formula (III):

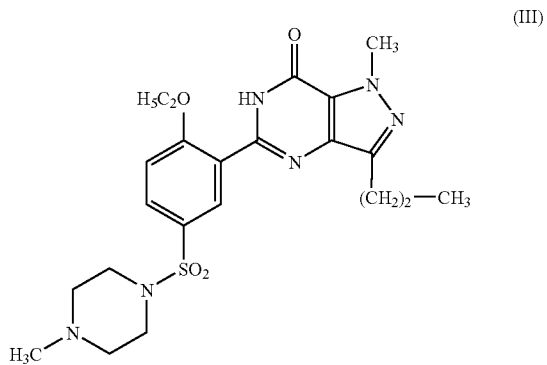

and is the compound known in the art under the generic name sildenafil for treatment of erectile dysfunctions.

Formula (III) compounds and their pharmaceutically acceptable salts can also be prepared in a known manner, e.g., in accordance with the method disclosed in EP 0 463 756.

It is to be expected that effective dosages for treatment of neuropathies will generally be in a similar or lower range as with known medical indications of compounds (1) and (3), respectively, i.e., they will typically be in the range from 1-100 mg/day, more specifically, 5-50 mg/day, and, typically, 25-50 mg/week.

The invention will be explained further by means of examples which are not limiting.

Example 1

A male patient (age 66 years) had been suffering from diabetes mellitus, type 2, for 9 years. While blood glucose values (HbA1c between 6 and 7%) were good, symptoms of a diabetic polyneuropathy appeared, namely vibration sensing of 2/8, no filament sensing, and a reduced hot/cold differentiation. Because of a simultaneous erectile dysfunction he was treated with sildenafil in its commercially available preparation (tablets) at 50 mg/week in a single administration.

Twelve months after start of therapy, a largely normal neurologic situation was reached, namely a vibration sensing of 5/8, intact filament sensing, and hot/cold differentiation. Subjectively, the patient noted disappearance of sensory misperceptions of temperature.

Example 2

A 61-year-old female patient had been suffering from diabetes mellitus, type 1, for about 35 years. Complications included a retinopathy and a painful neuropathy. Under intensified insulin therapy, blood glucose metabolism data were in a sub-optimum range (HbA1c around 8%). Thus, the patient suffered from a painful neuropathy and was treated unsuccessfully with various conventional medicaments.

After medication with sildenafil (50 mg/week, each in a single administration of the entire week's dosage), a lasting improvement of symptomatic pain was achieved in the course of the following three months. Objectifiable diagnostic data were improved as well.

What is claimed is:

1. A method for a chemotherapeutic treatment of a neuropathy characterized by administration to a patient suffering from neuropathy, from 1-100 mg/day of a pharmaceutical agent comprising a compound of formula (I):

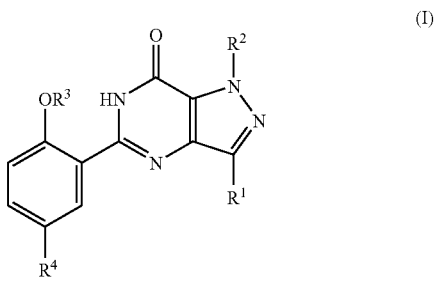

in which
$R^1 = C_{1-6}$alkyl, optionally substituted with halogen,
$R^2 =$ hydrogen or $C_{1-4}$alkyl, optionally substituted with halogen or replaced with halogen,
$R^3 = C_{2-4}$alkyl, optionally substituted with halogen,
$R^4 = SO_2NR^5R^6$,
$C_{1-4}$alkyl, optionally substituted with $NR^5R^6$, CN, $CONR^5R^6$, $CO_2R^7$, or halogen,
$C_{2-4}$-alkenyl, optionally substituted with $NR^5R^6$, $SONR^5R^6$, $CONR^5R^6$, $CO_2R^7$, or halogen,
$C_{2-4}$-alkanoyl, optionally substituted with $NR^5R^6$, $SONR^5R^6$, $CONR^5R^6$, $CO_2R^7$, or halogen,
$R^5$ and $R^6$, independent of one another, represent hydrogen or $C_{1-4}$alkyl, or, together with the nitrogen atom to which they are attached, represent a pyrrolidino, piperidino, morpholino, 4-($NR^8$)-1-piperazinyl or 1-imidazolyl ring which, optionally, may be substituted with one or two $C_{1-4}$alkyl groups,
$R^7 =$ hydrogen or $C_{1-4}$alkyl, optionally, substituted with fluorine, and
$R^8 =$ hydrogen, $C_{1-3}$alkyl, or hydroxy alkyl having 1-4 C atoms, or a pharmaceutically acceptable salt thereof,
wherein the neuropathy is selected from the group consisting of a peripheral diabetic polyneuropathy, gastroparesis, a toxic neuropathy, and a metabolic neuropathy.

2. The method of claim 1 wherein the pharmaceutical agent comprises a compound of formula (Ia):

(Ia)

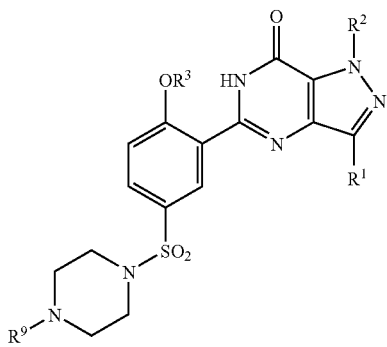

wherein $R^9$ is an alkyl group having 1-4 C atoms which, optionally, are substituted with halogen or replaced by halogen;
or a pharmaceutically acceptable salt thereof.

3. The method of claim 1 wherein the pharmaceutical agent comprises a compound of formula (III):

(III)

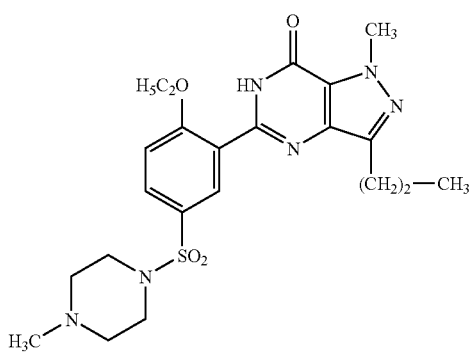

or a pharmaceutically acceptable salt thereof.

4. The method of claim 1, wherein from 5-50 mg/day of said pharmaceutical agent is administered to the patient being treated.

5. The method of claim 1, wherein from 25-50 mg/day of said pharmaceutical agent is administered to the patient being treated.

6. The method of claim 1 wherein the neuropathy is selected from the group consisting of gastroparesis, a toxic neuropathy, and a metabolic neuropathy.

7. A method for a chemotherapeutic treatment of a peripheral diabetic polyneuropathy consisting of administration to a patient suffering from the polyneuropathy, from 1-100 mg/day of a pharmaceutical agent comprising a compound of formula (I):

(I)

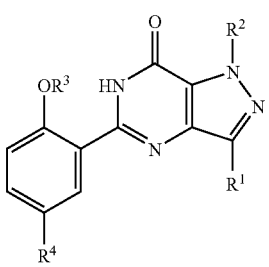

in which
$R^1 = C_{1-6}$alkyl, optionally substituted with halogen,
$R^2$=hydrogen or $C_{1-4}$alkyl, optionally substituted with halogen or replaced with halogen,
$R^3 = C_{2-4}$alkyl, optionally substituted with halogen,
$R^4 = SO_2NR^5R^6$,
$C_{1-4}$alkyl, optionally substituted with $NR^5R^6$, CN, $CONR^5R^6$, $CO_2R^7$, or halogen,
$C_{2-4}$-alkenyl, optionally substituted with $NR^5R^6$, $SONR^5R^6$, $CONR^5R^6$, $CO_2R^7$, or halogen,
$C_{2-4}$-alkanoyl, optionally substituted with $NR^5R^6$, $SONR^5R^6$, $CONR^5R^6$, $CO_2R^7$, or halogen,
$R^5$ and $R^6$, independent of one another, represent hydrogen or $C_{1-4}$alkyl, or, together with the nitrogen atom to which they are attached, represent a pyrrolidino, piperidino, morpholino, 4-($NR^8$)-1-piperazinyl or 1-imidazolyl ring which, optionally, may be substituted with one or two $C_{1-4}$alkyl groups,
$R^7$=hydrogen or $C_{1-4}$alkyl, optionally, substituted with fluorine, and
$R^8$=hydrogen, $C_{1-3}$alkyl, or hydroxy alkyl having 1-4 C atoms, or a pharmaceutically acceptable salt thereof.

* * * * *

UNITED STATES PATENT AND TRADEMARK OFFICE
CERTIFICATE OF CORRECTION

PATENT NO.         : 7,338,955 B1
APPLICATION NO. : 10/088113
DATED              : March 4, 2008
INVENTOR(S)       : Juerg Lareida It is certified that error appears in the above-identified patent and that said Letters Patent is hereby corrected as shown below:

On the Cover Page:

At field (57), line 4, "$R^{\&}$" should be -- $R^6$ --.

In the Specification:

At Column 2, line 12, "where," should be -- where --.

Signed and Sealed this

Nineteenth Day of August, 2008

JON W. DUDAS
*Director of the United States Patent and Trademark Office*